US012357733B2

(12) United States Patent
Hedmann et al.

(10) Patent No.: US 12,357,733 B2
(45) Date of Patent: Jul. 15, 2025

(54) PUMP SYSTEM, DIALYSIS MACHINE, AND METHOD OF OPERATING A PUMP

(71) Applicant: FRESENIUS MEDICAL CARE DEUTSCHLAND GMBH, Bad Homburg (DE)

(72) Inventors: Frank Hedmann, Volkach (DE); Sven Sebesta, Hausen (DE); Torsten Hochrein, Hausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 971 days.

(21) Appl. No.: 16/628,043

(22) PCT Filed: Jul. 3, 2018

(86) PCT No.: PCT/EP2018/068005
§ 371 (c)(1),
(2) Date: Jan. 2, 2020

(87) PCT Pub. No.: WO2019/007992
PCT Pub. Date: Jan. 10, 2019

(65) Prior Publication Data

US 2021/0138139 A1 May 13, 2021

(30) Foreign Application Priority Data

Jul. 4, 2017 (DE) ..................... 10 2017 114 895.7

(51) Int. Cl.
*A61M 1/14* (2006.01)
*A61M 1/16* (2006.01)
(Continued)

(52) U.S. Cl.
CPC ................ *A61M 1/14* (2013.01); *A61M 1/16* (2013.01); *A61M 1/1623* (2014.02);
(Continued)

(58) Field of Classification Search
CPC .......... A61M 1/14; A61M 1/15; A61M 1/152; A61M 1/1524; A61M 1/155; A61M 1/156;
(Continued)

(56) References Cited

U.S. PATENT DOCUMENTS 3,204,631 A 9/1965 Fields
4,710,166 A * 12/1987 Thompson ............ A61M 5/172 604/65
(Continued)

FOREIGN PATENT DOCUMENTS

CH 333650 A * 10/1958 ............ F04B 49/121
CN 103352833 10/2013
(Continued)

OTHER PUBLICATIONS

English translation of WO 2013/045711 (Year: 2013).*

*Primary Examiner* — Shefali D Patel
(74) *Attorney, Agent, or Firm* — Jacobson Holman PLLC

(57) ABSTRACT

A pump system for generating a volume flow of a dialysis solution in a dialysis machine, the pump system includes at least one piston pump having a piston that cooperates with a working fluid, which exerts a force on a conveying means, and in particular on a membrane. The pump system includes setting means, with which a conveying volume of the at least one piston pump per piston stroke can be reduced, with the setting means having at least one of a position-variable mechanical piston stop to reduce the piston stroke, means to reduce a quantity of the working fluid, and means to reduce a volume of a conveying chamber that cooperates with the conveying means and that contains the dialysis solution to be conveyed.

14 Claims, 3 Drawing Sheets

(51) Int. Cl.

| | |
|---|---|
| *A61M 1/28* | (2006.01) |
| *F04B 43/02* | (2006.01) |
| *F04B 43/067* | (2006.01) |
| *F04B 45/04* | (2006.01) |
| *F04B 45/053* | (2006.01) |
| *F04B 49/14* | (2006.01) |

(52) U.S. Cl.
CPC .......... *A61M 1/155* (2022.05); *A61M 1/1561* (2022.05); *A61M 1/159* (2022.05); *A61M 1/281* (2014.02); *F04B 43/026* (2013.01); *F04B 43/067* (2013.01); *F04B 45/043* (2013.01); *F04B 45/0533* (2013.01); *F04B 49/14* (2013.01)

(58) Field of Classification Search
CPC ...... A61M 1/1562; A61M 1/159; A61M 1/16; A61M 1/1601; A61M 1/1621; A61M 1/1623; A61M 1/1631; A61M 1/26; A61M 1/267; A61M 1/28; A61M 1/281; A61M 1/282; A61M 2005/14506; A61M 2205/12; A61M 2205/123; A61M 2205/3379; A61M 2205/50; A61M 2205/502; A61M 2205/505; A61M 5/142; A61M 5/145; A61M 5/1452; A61M 5/14586; A61M 5/14593; A61M 5/155; A61M 5/16877; F04B 13/00; F04B 43/02; F04B 43/021; F04B 43/06; F04B 43/067; F04B 45/04; F04B 45/053; F04B 45/0533; F04B 49/12; F04B 49/14; F04B 49/16; F04B 9/02
See application file for complete search history.

(56) References Cited

U.S. PATENT DOCUMENTS

| | | | | |
|---|---|---|---|---|
| 5,983,777 | A | 11/1999 | Cassaday | |
| 6,905,479 | B1 * | 6/2005 | Bouchard ............. | A61M 60/37 604/151 |
| 7,935,074 | B2 * | 5/2011 | Plahey .................. | A61M 1/281 604/29 |
| 2003/0136189 | A1 | 7/2003 | Lauman et al. | |
| 2013/0006171 | A1 | 1/2013 | Griessmann et al. | |

FOREIGN PATENT DOCUMENTS

| | | |
|---|---|---|
| DE | 19742632 | 4/1999 |
| DE | 19919572 | 11/2000 |
| WO | WO2013/045711 | 4/2013 |
| WO | WO2016/059614 | 4/2016 |

* cited by examiner

PUMP SYSTEM, DIALYSIS MACHINE, AND METHOD OF OPERATING A PUMP

CROSS-REFERENCE TO RELATED APPLICATIONS

This application is a 371 of PCT/EP2018/068005, filed Jul. 3, 2018, and claims foreign priority to DE 10 2017 114 895.7, filed Jul. 4, 2017.

BACKGROUND OF THE INVENTION

1. Field of the Invention

The invention relates to a pump system for setting a volume flow, preferably a continuous volume flow, of dialysis solution in a dialysis machine, to a dialysis machine, preferably a peritoneal dialysis machine, having such a pump system, and to a method of conveying a dialysis solution.

2. Description of Related Art

Various dialysis methods are known from the prior art. During automatic peritoneal dialysis a peritoneal dialysis machine controls the introduction of the fresh dialysis solution into the abdominal cavity and the draining of the consumed dialysis solution from the abdominal cavity.

Gravimetric devices can be used to generate the flow of dialysis solution, i.e. those in which the flow is effected by gravity and also those devices in which pumps are used for conveying the dialysis solution.

Piston pumps are frequently used in this context. As can be seen from FIG. 1, a known pump system comprises a piston 8 that is arranged in a cylindrical space and this is connected to a piston rod that is in turn driven by a motor-powered pinion 7. The pinion 7 cooperates with the gear rack portion of the piston rod such that the piston rod is moved to the left or to the right, i.e. in the conveying direction or in the intake region, depending on the direction of rotation of the pinion in accordance with FIG. 1.

The piston 8 is in contact with a working fluid that is marked by a dashed line and that fills the working space of the cylindrical space on the side of the piston that is remote from the piston rod, as well as a line section adjoining it and finally a chamber 4 that is closed by a membrane on one side.

The membrane 9 contacts a flexible film or membrane of the cassette 3 that is designed as a disposable article. The membrane 9 can in this respect be produced e.g. from silicone. By application of an overpressure in the chamber 4, the membrane 9, and with it the flexible film, is pressed into the pump chamber 3 of the cassette. If in contrast a vacuum is applied to the chamber 4 in that the piston 8 is moved to the left, the membrane 9 is, however, pulled into the chamber 4. Due to the vacuum between the flexible film and the membrane, the flexible film follows this movement so that the volume of the pump chamber 3 increases.

The movement of the piston can be recorded via the position encoder. It can hereby be determined how much hydraulic fluid was pressed into the chamber 4 and how much hydraulic fluid was removed from it. Pressure sensors 5 are furthermore provided at the hydraulic system which measure the pressure in the hydraulic system. They on the one hand allow a functional check of the hydraulic system since the data of the pressure sensors can be compared with those of the position encoder 6 and the leak tightness of the hydraulic system can hereby be checked.

In addition, the pressure sensors allow a determination of the pressure in the pump chamber 3 of the cassette. If the hydraulic pump is not moved, a pressure equilibrium is adopted between the chamber 4 and the pump chamber 3. The pressure of the hydraulic fluid then corresponds to the pressure in the pump chamber 3.

Pumps of peritoneal dialysis machines convey volumes in the range from 25 ml to 3500 ml in the inflow of the dialysis solution into the abdomen of the patient. Tolerances of up to 10% have to be expected for construction reasons, which may result in an overfill of 2.5 ml with a minimal inflow volume of 25 ml. Apart from this, a defect in the performance drivers of the pump can have the result that a complete chamber was administered despite a different prescription, i.e. the maximum possible piston path was run through and thus a maximum possible volume was administered. If a comparatively small inflow volume was prescribed, this can result in a considerable overfill of the patient. This can in turn have the consequence of a danger to the patient that cannot be compensated by measures of functional safety.

SUMMARY OF THE INVENTION

It is thus the underlying object of the present invention to further develop a pump system of the initially named kind such that the probability of an overfill of the patient is reduced with respect to known systems.

This object is achieved by a pump system as described herein.

Provision is accordingly made that the pump system has setting means by which the conveying volume of the piston pump per piston stroke can be reduced, with the setting means comprising a position-variable mechanical piston stop to reduce the piston stroke and/or means to reduce the quantity of the work fluid and/or means to reduce the volume of the conveying chamber that cooperates with the conveying means and that contains the dialysis solution to be conveyed.

The underlying idea of the invention in an embodiment is thus to limit the travel distance of the piston of the pump and thus the conveying volume per piston stroke by a mechanical abutment. The abutment is preferably located at the end of the chamber, i.e. at the end of the working space at the expulsion side in which the piston is movably received. The bounding of the travel path of the piston brings along the advantage that small volumes can also be conveyed at high precision.

The volume of dialysis fluid conveyable per piston stroke is limited by this measure such that no overfill of the patient occurs even on a defect in the power electronics.

The abutment is positionable at different points and is preferably also settable or removable such that the piston can also again run through the complete, i.e. maximum, travel path to be able to convey a maximum conveying volume per piston stroke.

Provision is made in a further embodiment that the setting means are formed by means to reduce the volume of the working fluid that the piston sets into movement to deflect the membrane and thus to effect the conveying of the dialysis solution. The volume of the working fluid can thus be reduced by this means, for example in that some of the working fluid is led off into a storage container. If more working fluid is again required, its volume can again be increased accordingly.

Since the quantity or volume of the working fluid in the pump system determines the maximum conveying volume, the conveying volume per piston stroke can be varied by adapting this quantity or volume.

The determination of the quantity or volume can generally be derived from the prescribed inflow volume of the dialysis solution. It is thus possible to reduce the volume of the working fluid for a complete treatment so that only a correspondingly reduced quantity of dialysis solution is permanently conveyed per piston stroke or it is possible to configure this volume only for the last pump stroke or strokes of an inflow.

This procedure is not only conceivable on the change of the volume of the working fluid, but also for the further alternatives of the setting means.

Provision is made in a further embodiment that the setting means form means to reduce the volume of the conveying chamber that cooperates with the conveying means of the pump system and that contains the dialysis solution to be conveyed.

The conveying chamber is preferably a component of a disposable, i.e. of a disposable article, that cooperates with the dialysis machine such that the membrane or another conveying member of the pump system cooperates with a membrane that bounds the conveying chamber of the disposable. The membrane of the pump system thus cooperates with the membrane of the disposable.

If a membrane of the pump system is deflected by a piston stroke, a corresponding movement of the membrane of the conveying chamber takes place and thus a corresponding conveying of the dialysis solution.

A restriction of the pump stroke is thus also possible in that a spatial limitation of the conveying chamber of the cassette, i.e. of the disposable, is carried out. This can be achieved, for example, in that, with respect to a starting state in which higher conveying rates are desired, a cassette having a greater wall thickness or having a volume reduced in a different manner is used.

Ultimately, a reduction of the piston stroke can thus also be achieved by a reduction of the conveying volume of the cassette or of the conveying chamber, which likewise improves the accuracy of the conveying of the dialysis solution. A mechanical abutment thus does not necessarily have to be provided in the pump system. A reduction of the piston stroke can also be implemented by a reduction of the conveying volume of the chamber with which the membrane of the pump system cooperates.

The pump system can have any desired piston pump, for example a hydraulic piston pump or also a pneumatic piston pump. The working fluid can thus be a liquid or a gas.

Input means are provided in a further embodiment of the invention by which the total desired conveying volume or the desired conveying volume from a specific point in time onward or the desired conveying volume per piston stroke can be input and the setting means are connected to the input means such that the setting means are set in dependence on the values input into the input means.

It is thus conceivable, for example, that the user of the pump system specifies a desired conveying volume, e.g. 5 I dialysis solution. The input means can be formed, for example, by a touch screen or by a keyboard or the like. It is also conceivable that the user of the pump system only inputs the desired conveying volume to be administered from a specific point in time onward. If, for example, the total volume of the dialysis solution to be administered is 5 I, provision can be made that 1 I still has to be administered after the administration of 4 I has been input by the user.

It is conceivable in an embodiment that the user inputs the desired conveying volume per piston stroke.

The pump system determines the conveying volume per piston stroke in dependence on the input data and sets it with the aid of the setting means. It is, for example, conceivable that the first four liters are administered with a comparatively large conveying volume per piston stroke and the remaining last liter is administered with a conveying volume per piston stroke smaller in comparison therewith. This setting can be carried out by the pump system or by the dialysis machine or also manually.

It generally applies that the pump system can also be designed such that an independent determination is made as to which conveying volume is set per piston stroke. The pump system can, for example, set this setting in dependence on the treatment time, on the volume of dialysis solution to be administered in total or on the volume of dialysis solution still to be administered, etc. In this case, the above-named input means to be actuated by a user can be dispensed with.

The setting means and the pump system can be configured such that the conveying volume per piston stroke is constant over the total conveying time. If the conveying volume of the dialysis solution to be administered in total is small, it is sensible to set a conveying means per piston stroke that is as small as possible.

It is preferred if the setting means and the pump means are configured such that the conveying volume per piston stroke is variable and is in particular smaller toward the end of the conveying procedure than at the start of the conveying procedure. It is thus possible to administer comparatively large conveying volumes at the start of the administration of dialysis solution, which represents a time saving, and to reduce the conveying volume per piston stroke or to set it to a smaller value toward the end of the administration procedure when only a comparatively small residual volume still has to be conveyed to the patient, which has the above-named advantage of a more precise conveying and of an avoidance of an overfill of the patient.

It is furthermore conceivable that the setting means are configured such that the quantity of the working fluid is reducible, with provision being made that the quantity of the working fluid is reduced, starting from a starting state, such that the influence of the membrane tension on the patient pressure and/or on the pressure of the working fluid is smaller than in the starting state. The smaller the membrane voltage, the smaller its influence on the measured pressure in the working fluid. In the equilibrium state, when no conveying through the pump system takes place, the measured pressure in the working fluid corresponds to that in the conveying chamber so that a conclusion can be drawn on the patient pressure, i.e. on the pressure in the dialysis solution administered to the patient.

The setting of the quantity or of the volume of the working fluid can thus be used, for example, to shift the behavior of the membrane from the working region of the piston pump into the abutment region. The detection of the patient pressure can thus be positively influenced and falsifications due to the membrane tension can be removed.

The pump of the pump system preferably has a piston space that is in communication via a hose with a chamber that is limited by the membrane. The membrane in turn preferably acts on a cassette designed as a disposable or on its conveying chamber, whereby the conveying volume is led to the patient.

To achieve a continuous or largely continuous flow of dialysis solution, the pump system preferably has two piston pumps that work in a staggered manner.

It is pointed out at this point that the terms ""a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

The present invention furthermore relates to a dialysis machine, in particular to a peritoneal dialysis machine, with the dialysis machine having a pump system as described herein.

The invention further relates to a method of conveying a dialysis solution by means of a piston pump whose piston cooperates with a working fluid that in turn exerts a force on a conveying means, in particular on a membrane, with the conveying volume per piston stroke being reduced for the purpose of increasing the conveying precision of the piston pump in that a piston abutment is changed such that the piston stroke is reduced and/or in that the quantity of the working fluid is reduced and/or in that the volume of the conveying chamber that cooperates with the conveying means and that includes the dialysis solution is reduced.

It is preferred if the total desired conveying volume or the desired conveying volume from a specific point in time onward or the desired conveying volume per piston stroke is input into input means and the reduction of the conveying volume is reduced in dependence on the value or values input into the input means. As stated above, it is also conceivable that such input means are dispensed with and the pump system or the dialysis machine itself determines which conveying volume is set per piston stroke from which point in time onward.

The conveying volume per piston stroke can be kept constant over the total conveying duration or can be varied, with provision preferably being made that the conveying volume per piston stroke is smaller toward the end of the conveying procedure than at the start of the conveying procedure to make the precision in the conveying of the then comparatively small residual conveying volume as high as possible.

BRIEF DESCRIPTION OF THE DRAWINGS

Further details and advantages of the invention will be explained in more detail with reference to an embodiment shown in the drawing.

There are shown:

FIG. 4 illustrates an embodiment of the inventive pump system for generating a volume flow of a dialysis solution in a dialysis machine, and illustrates, in addition to the elements shown in FIG. 1, a setting means 20, a piston stop 30, an input means 40, a calculation means 50, a means to reduce a quantity of working fluid 60, and a fluid line 70.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
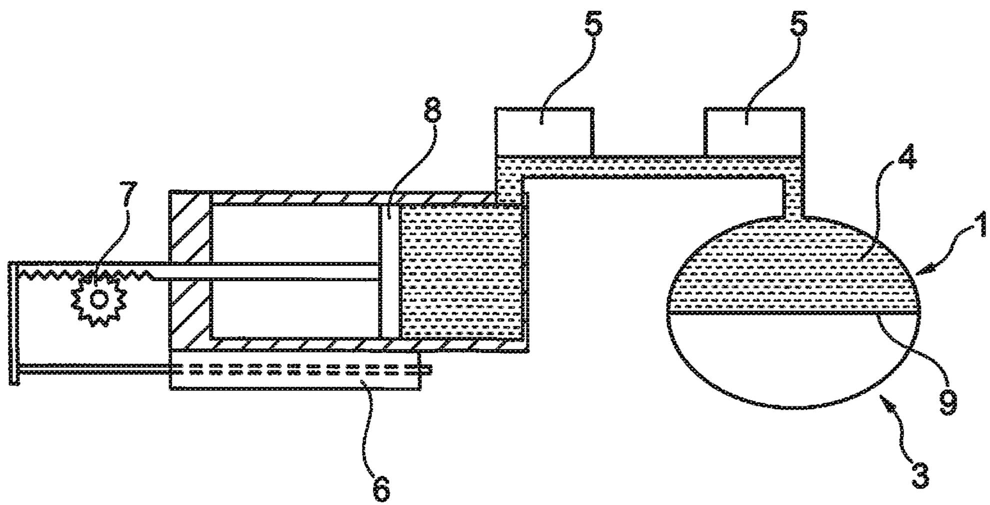
FIG. 1: a schematic view of a pump system.

FIG. 1 shows a pump system that is known from the prior art, but that can also be used as part of the present invention, i.e. that is also in accordance with the invention. Reference is therefore made to the above statements on FIG. 1.

The reduction of the conveying volume per piston stroke can take place by a mechanical piston abutment, not shown, preferably at the base, i.e. in the region of the chamber end in which the piston moves. An alternative is the reduction of the volume of the hydraulic fluid or of another working fluid that extends between the piston and the membrane and that transmits the movement of the piston onto the membrane. To vary the volume, a storage container and a valve can be provided that make it possible that the working medium is received in the hydraulic circuit, etc. or is removed therefrom. These components are currently used to degas the working fluid and thus to achieve a maximum, best-possible travel path of the piston.

The invention is generally not limited to carrying out a reduction of the volume conveyed per piston stroke, but rather an increase of this volume can naturally also again be carried out if it is desired.

A further alternative of the setting comprises the reduction of the volume of a cassette, etc. that cooperates with the membrane of the pump system and that contains the dialysis solution.

Figure 2:
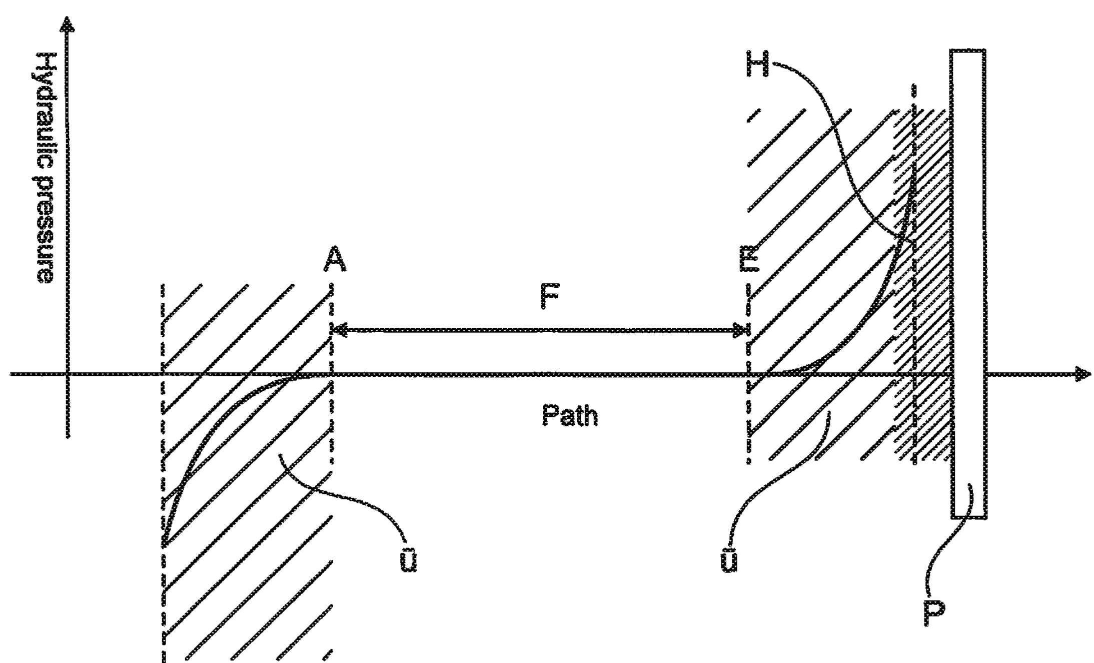
FIG. 2: a diagram to represent the pressure progression in the working fluid.

The hydraulic pressure in the working fluid over the path of the piston is entered on FIG. 2.

The hatched regions mark the ramping up, i.e. the increase of the piston speed, and the ramping down, i.e. the reduction of the piston speed. In these regions marked by Ü, both pumps work alternately so that the hatched regions represent overlap regions of the operation of two pumps.

The start of the chamber in which the piston is received in a manner movable to and fro is marked by A and the end of the chamber is marked by E. F represents the chamber region that is relevant to the conveying and that is variably settable. The region of the hydraulic medium to be displaced is marked by H.

P represents the pump plate, i.e. the membrane, etc., which acts on the membrane of the conveying chamber of the disposable.

Exactly one pump can be used in accordance with the invention. The case is, however, also covered by the invention that two pumps or more than two pumps are present.

Figure 3:
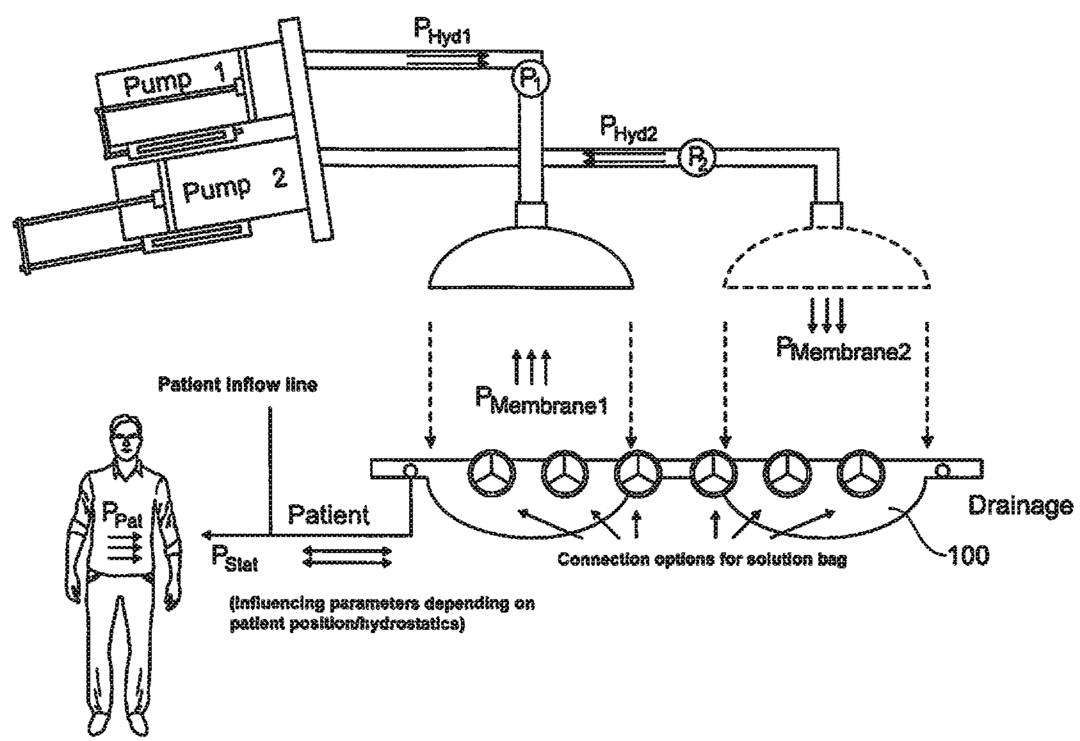
FIG. 3: a further schematic diagram of the pump system of a peritoneal dialysis machine.
Figure 4:
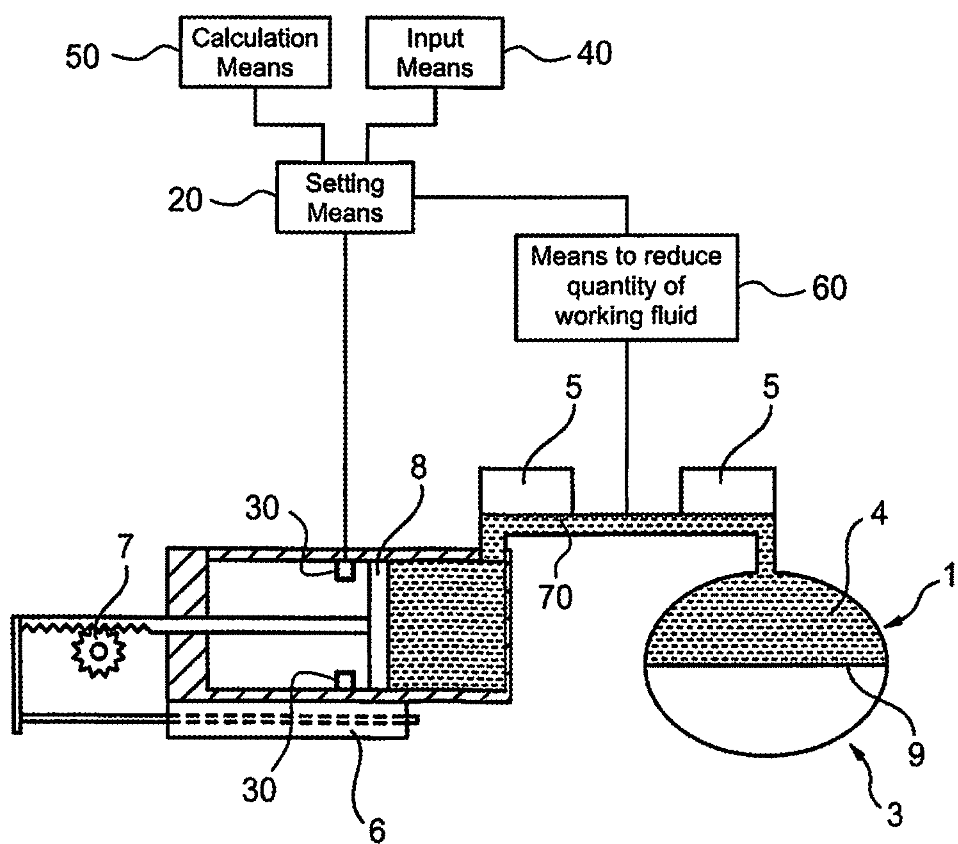
FIG. 4 is a schematic illustration of a pump system according to an embodiment of the instant invention. More specifically.

FIG. 3 shows a peritoneal dialysis machine or system known from the prior art.

As can be seen from FIG. 3, two membrane pumps (pump 1, pump 2) are typically used that each have a position encoder to be able to determine the piston position. The membrane pumps act on pump chambers 100 by which dialyzate is pumped out of correspondingly present dialyzate bags into the abdominal cavity of a patient or by which consumed dialyzate is drained from the abdominal cavity of the patient. To achieve a constant dialyzate volume flow despite the discontinuously working membrane pump, the hydraulic pressure $P_{Hyd}$ in the hydraulic lines is determined. In the event that the membrane pumps are pneumatically driven, the corresponding pneumatic pressure in the lines is determined. To ensure a pressure monitoring, the pressures $P_{Hyd}$ measured by means of the pressure sensors are compensated by some influencing factors. It is in this respect the respective membrane pressure $P_{Membrane}$, on the one hand, i.e. the counter-pressure that is caused in response to the measured hydraulic pressure $P_{Hyd}$ due to the deflection and inherent tension of the membrane. As the deflection increases, the membrane tension increases disproportionally and is accompanied by a construction-induced speed response. This counter-pressure depends on the position of the hydraulic pump that is typically measured via a position encoder. The counter-pressure that arises due to the flow resistance in the system, i.e. in the pump and in the pump chamber configured as a disposable, is furthermore taken into account as a further compensation factor. This counter-pressure to be taken into account depends on the speed in the system. Finally, the hydrostatic pressure $P_{Stat}$ has to be taken into account that results due to the position of the patient.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A pump system for generating a volume flow of a dialysis solution in a dialysis machine, said pump system comprising:
- a first piston pump and a second piston pump, each of the first piston pump and the second piston pump having a piston that cooperates with a working fluid which exerts a force on a conveying means that is a membrane, the first piston pump and the second piston pump being configured so as to operate in a staggered manner;
- setting means with which to, alternatively, reduce and increase, a conveying volume of the first piston pump and the second piston pump per piston stroke,
- the setting means including at least one of a piston stop to, alternatively, reduce and increase, the piston stroke, the piston stop being located in a piston chamber in which the piston moves, and
- means to, alternatively, reduce and increase, a quantity of the working fluid, the means to alternatively reduce and increase the quantity of the working fluid including a storage container for storing the working fluid, and a valve that enables a volume of the working fluid to alternatively be reduced and increased;
- calculation means with which to determine a residual desired conveying volume from a specific point in time onward; and
- input means or calculation means with which to input or determine a total desired conveying volume or a desired conveying volume per piston stroke, with the setting means being connected to the input means or to the calculation means with which to input or determine the total desired conveying volume or the desired conveying volume per piston stroke such that the setting means is configured to set the conveying volume of the first piston pump and the second piston pump per piston stroke in dependence on values input into the input means or determined by the calculation means with which to input or determine the total desired conveying volume or the desired conveying volume per piston stroke.

2. The pump system in accordance with claim 1, wherein the working fluid is a liquid or a gas.

3. The pump system in accordance with claim 1, wherein the setting means is configured such that the conveying volume per piston stroke is constant over a total conveying time.

4. The pump system in accordance with claim 1 wherein the setting means is configured such that the conveying volume per piston stroke is variable over a conveying time.

5. The pump system according to claim 4, wherein the conveying volume per piston stroke is smaller toward an end of a conveying procedure than at a start of the conveying procedure.

6. The pump system in accordance with claim 1, wherein the setting means is configured such that the quantity of the working fluid is reduced, starting from a starting state, such that an influence of a tension of the membrane on at least one of a patient pressure and a pressure of the working fluid, is smaller than in the starting state.

7. The pump system in accordance with claim 1, wherein the piston chamber of each of the first piston pump and the second piston pump is in communication via a fluid line with a chamber that is bounded by the membrane.

8. A dialysis machine, said dialysis machine comprising the pump system in accordance with claim 1.

9. The dialysis machine according to claim 8, wherein the dialysis machine is a peritoneal dialysis machine.

10. A method of conveying a dialysis solution with a pump system, said pump system comprising:
- a first piston pump and a second piston pump, each of the first piston pump and the second piston pump having a piston that cooperates with a working fluid which exerts a force on a conveying means that is a membrane, the first piston pump and the second piston pump being configured so as to operate in a staggered manner;
- setting means with which to, alternatively, reduce and increase, a conveying volume of the first piston pump and the second piston pump per piston stroke,
- the setting means including at least one of a piston stop to, alternatively, reduce and increase, the piston stroke, the piston stop being located in a piston chamber in which the piston moves, and
- means to, alternatively, reduce and increase, a quantity of the working fluid, the means to alternatively reduce and increase the quantity of the working fluid including a storage container for storing the working fluid, and a valve that enables a volume of the working fluid to alternatively be reduced and increased;
- calculation means with which to determine a residual desired conveying volume from a specific point in time onward; and
- input means or calculation means with which to input or determine a total desired conveying volume or a desired conveying volume per piston stroke, with the setting means being connected to the input means or to the calculation means with which to input or determine the total desired conveying volume or the desired conveying volume per piston stroke such that the setting means is configured to set the conveying volume of the first piston pump and the second piston pump per piston stroke in dependence on values input into the input means or determined by the calculation means with which to input or determine the total desired conveying volume or the desired conveying volume per piston stroke, said method comprising:
- alternatively, reducing and increasing the conveying volume per piston stroke to increase a conveying precision of the first piston pump and the second piston pump by at least one of changing the piston stop such that the piston stroke is alternatively reduced and increased, and, alternatively, reducing and increasing the quantity of the working fluid.

11. The method in accordance with claim 10, wherein the total desired conveying volume or the desired conveying volume from a specific point in time onward, or the desired conveying volume per piston stroke, is input into the input means or is determined by the calculation means with which to input or determine the total desired conveying volume or the desired conveying volume per piston stroke; and the reduction of the conveying volume is set in dependence on values input into the input means or determined by the calculation means with which to input or determine the total desired conveying volume or the desired conveying volume per piston stroke.

12. The method in accordance with claim 10, wherein the conveying volume per piston stroke is kept constant over the total conveying time or is varied over the conveying time.

13. The method according to claim 12, wherein the conveying volume per piston stroke is smaller toward an end of a conveying procedure than at a start of the conveying procedure.

14. The method according to claim 10, wherein the alternative reducing and increasing of the quantity of the working fluid is effected with the storage container for storing the working fluid, and the valve that enables the volume of the working fluid to be alternatively reduced and increased.

* * * * *